(12) United States Patent
Tsai et al.

(10) Patent No.: US 11,494,698 B2
(45) Date of Patent: Nov. 8, 2022

(54) METHOD AND ELECTRONIC DEVICE FOR SELECTING INFLUENCE INDICATORS BY USING AUTOMATIC MECHANISM

(71) Applicants: Acer Incorporated, New Taipei (TW); National Yang-Ming University, Taipei (TW)

(72) Inventors: Zong-Han Tsai, New Taipei (TW); Tsung-Hsien Tsai, New Taipei (TW); Liang-Kung Chen, Taipei (TW); Li-Ning Peng, Taipei (TW); Ting-Fen Tsai, Taipei (TW); Chi-Hung Lin, Taipei (TW); Chien-Yi Tung, Taipei (TW); Wei-Ju Lin, Taipei (TW)

(73) Assignees: Acer Incorporated, New Taipei (TW); National Yang-Ming University, Taipei (TW)

(*) Notice: Subject to any disclaimer, the term of this patent is extended or adjusted under 35 U.S.C. 154(b) by 384 days.

(21) Appl. No.: 16/816,282

(22) Filed: Mar. 12, 2020

(65) Prior Publication Data

US 2021/0209503 A1    Jul. 8, 2021

(30) Foreign Application Priority Data

Jan. 6, 2020  (TW) ................. 109100302

(51) Int. Cl.
*G06N 3/00*    (2006.01)
*G06N 20/00*   (2019.01)
(Continued)

(52) U.S. Cl.
CPC ............... *G06N 20/00* (2019.01); *G06N 5/04* (2013.01); *G06F 17/18* (2013.01); *G06N 3/08* (2013.01); *G06N 5/02* (2013.01); *G06N 7/00* (2013.01)

(58) Field of Classification Search
CPC ............ G06N 20/00; G06N 5/04; G06N 5/03; G06N 5/02; G06N 7/00; G06F 17/18
See application file for complete search history.

(56) References Cited

U.S. PATENT DOCUMENTS

| 2003/0207278 A1 | 11/2003 | Khan et al. |
| 2018/0039732 A1 | 2/2018 | Szeto et al. |
| 2022/0036223 A1* | 2/2022 | Eto ..................... G06N 7/00 |

FOREIGN PATENT DOCUMENTS

| CN | 101794354 | 8/2010 |
| CN | 103705225 | 4/2014 |

(Continued)

OTHER PUBLICATIONS

Isabelle Guyon et al., "An introduction to variable and feature selection," Journal of Machine Learning Research, vol. 3, Mar. 2003, pp. 1157-1182.

(Continued)

*Primary Examiner* — Joseph J Lauture
(74) *Attorney, Agent, or Firm* — JCIPRNET (57) ABSTRACT

A method and an electronic device for selecting influence indicators by using an automatic mechanism are provided. The method includes following steps. Raw data is obtained, where the raw data includes a body-related variable and a plurality of to-be-measured indicators corresponding to the body-related variable. The body-related variable is set as a target parameter. The body-related variable and the to-be-measured indicators are input into a plurality of validation models, and the to-be-measured indicators are sorted according an output result of the validation models to obtain ranking data. Importance of the to-be-measured indicators is calculated by using a screening condition according to the ranking data, so as to select a candidate indicator from the to-be-measured indicators. An influence indicator is deter- (Continued)

mined by calculating a correlation between the candidate indicator and the body-related variable.

10 Claims, 4 Drawing Sheets

(51) Int. Cl.
  *G06N 5/04* (2006.01)
  *G06N 3/08* (2006.01)
  *G06F 17/18* (2006.01)
  *G06N 5/02* (2006.01)
  *G06N 7/00* (2006.01)

(56) References Cited

FOREIGN PATENT DOCUMENTS

| | | |
|---|---|---|
| CN | 109460825 | 3/2019 |
| RU | 2666119 | 9/2018 |
| TW | 201217788 | 5/2012 |
| TW | I598444 | 9/2017 |
| TW | I630501 | 7/2018 |

OTHER PUBLICATIONS

"Search Report of Europe Counterpart Application", dated Sep. 11, 2020, p. 1-p. 10.

* cited by examiner

METHOD AND ELECTRONIC DEVICE FOR SELECTING INFLUENCE INDICATORS BY USING AUTOMATIC MECHANISM

CROSS-REFERENCE TO RELATED APPLICATION

This application claims the priority benefit of Taiwan application serial no. 109100302, filed on Jan. 6, 2020. The entirety of the above-mentioned patent application is hereby incorporated by reference herein and made a part of this specification.

BACKGROUND

Technical Field

The disclosure relates to an automatic selecting technology, and in particular, to a method for selecting influence indicators by using an automatic mechanism, and an electronic device capable of performing a function of selecting influence indicators by using an automatic mechanism.

Description of Related Art

Generally, senior people have less muscle mass than young people, and as people age, it is more easily for them to lose muscle mass. Excessive muscle loss easily triggers sarcopenia, which may be prevented at an early stage by researching the relationship between proteins and the muscle mass in human bodies and finding certain proteins for predicting the muscle mass so as to delay the aging speed.

However, of the significant amount of time and money may be consumed if the proteins are one by one analyzed through conducting experiments to learn whether the proteins are associated with the muscle mass. Accordingly, researches should concentrate on a technology for selecting a protein with influence.

SUMMARY

The disclosure provides a method and an electronic device for selecting influence indicators by using an automatic mechanism, so as to select an influence indicator from a plurality of to-be-measured indicators.

An embodiment of the disclosure provides a method for selecting influence indicators by using an automatic mechanism, and the method is adapted to an electronic device. The method for selecting the influence indicators by using the automatic mechanism includes following steps. Raw data is obtained, where the raw data includes a body-related variable and a plurality of to-be-measured indicators corresponding to the body-related variable. The body-related variable is set as a target parameter. The body-related variable and the to-be-measured indicators are input into a plurality of validation models, and the to-be-measured indicators are sorted according an output result of the validation models to obtain ranking data. Importance of the to-be-measured indicators is calculated by using a screening condition according to the ranking data to select a candidate indicator from the to-be-measured indicators. An influence indicator is determined by calculating a correlation between the candidate indicator and the body-related variable.

From another point of view, an embodiment of the disclosure provides an electronic device, and the electronic device includes a storage device and a processor. The storage device stores at least one instruction, and the processor is coupled to the storage device and is configured to execute the at least one instruction to perform following steps. Raw data is obtained, where the raw data includes a body-related variable and a plurality of to-be-measured indicators corresponding to the body-related variable. The body-related variable is set as a target parameter. The body-related variable and the to-be-measured indicators are input into a plurality of validation models, and the to-be-measured indicators are sorted according an output result of the validation models to obtain ranking data. Importance of the to-be-measured indicators is calculated by using a screening condition according to the ranking data to select a candidate indicator from the to-be-measured indicators. An influence indicator is determined by calculating a correlation between the candidate indicator and the body-related variable.

Based on the foregoing, in the method and the electronic device for selecting the influence indicators by using the automatic mechanism as provided in one or more embodiments of the disclosure, different body-related variables are set as the target parameters, and the body-related variables and the to-be-measured indicators corresponding to the body-related variables are input into the validation models, so that the to-be-measured indicators are sorted according to the output result of the validation models to obtain the ranking data. The to-be-measured indicators of high importance are selected by using the screening condition according to the ranking data, and then the correlation between the candidate indicator and the body-related variables is calculated to validate whether the candidate indicator has influence on the body-related variables. Therefore, the influence indicator correlated with the body-related variables may be selected from the to-be-measured indicators.

DESCRIPTION OF THE EMBODIMENTS

Some embodiments of the disclosure are to be described in detail with reference to the accompanying drawings. The component symbols cited in the following description are to be considered as the same or similar components when the same component symbol occurs in different accompanying drawings. The embodiments are only a part of the disclosure, and do not disclose all implementations of the disclosure. More precisely, the embodiments are merely examples of methods and electronic devices within the scope of the patent application of the disclosure.

Figure 1:
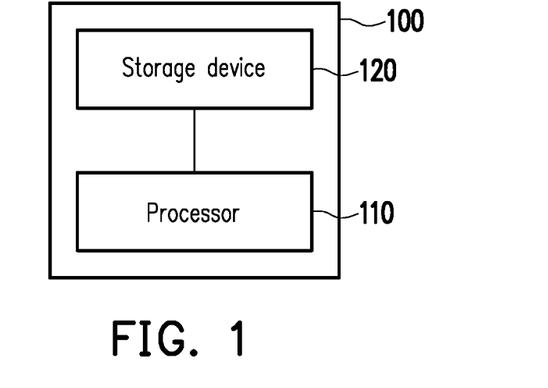
FIG. 1 is a block diagram of an electronic device according to an embodiment of the disclosure.

FIG. 1 is a block diagram of an electronic device according to an embodiment of the disclosure. With reference to FIG. 1, the electronic device 100 includes but is not limited to a processor 110 and a storage device 120. The processor 110 is coupled to the storage device 120, and may store and execute instructions recorded in the storage device 120, so as to implement a method for selecting influence indicators by using an automatic mechanism of the present embodiment of the disclosure. The electronic device 100 is, for example, an electronic device with a computing capability such as a personal computer (PC), a work station, a server, a notebook, a personal digital assistant (PDA), a smart phone, and a tablet personal computer (tablet PC), which is not limited in the disclosure.

In different embodiments, the processor 110 is, for example, a central processing unit (CPU) or another programmable general-purpose or special-purpose microprocessor, a digital signal processor (DSP), a programmable controller, an application-specific integrated circuit (ASIC), a programmable logic device (PLD), or another similar device, or a combination of the devices, which is not limited in the disclosure.

The storage device 120 is, for example, any type of fixed or removable random access memory (RAM), read-only memory (ROM), flash memory, or hard disk, or another similar device or a combination of the devices, and is configured to store one or more instructions that can be executed by the processor 110. The instructions may be loaded into the processor 110.

Figure 2:
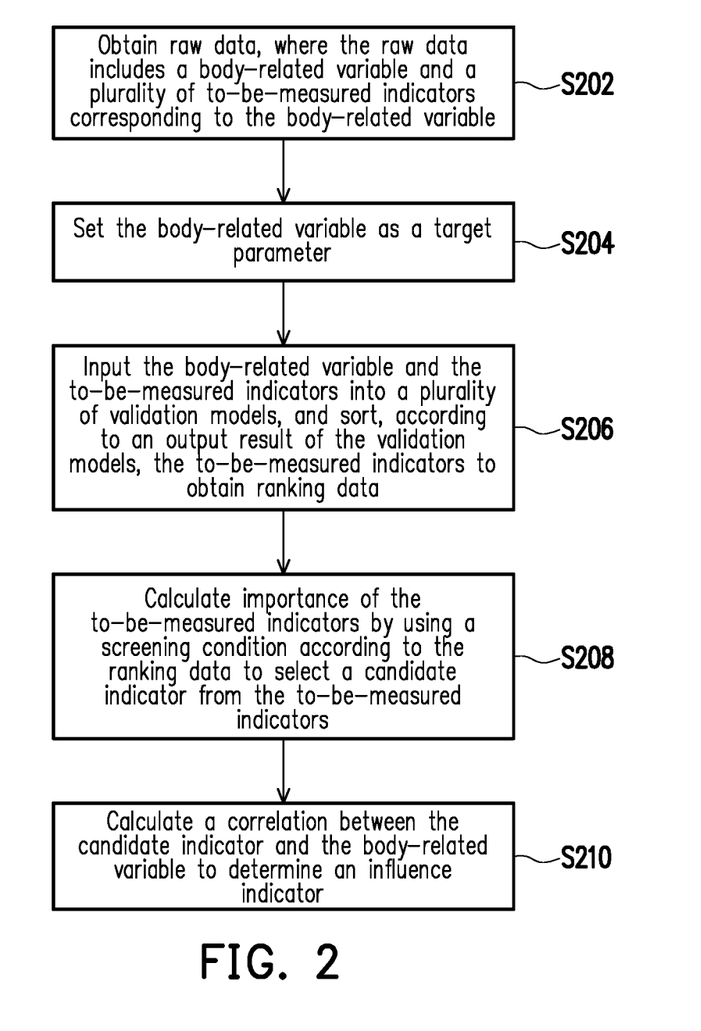
FIG. 2 is a flowchart of a method for selecting influence indicators by using an automatic mechanism according to an embodiment of the disclosure.

FIG. 2 is a flowchart of a method for selecting influence indicators by using an automatic mechanism according to an embodiment of the disclosure. Referring FIG. 1 and FIG. 2, the method of the present embodiment is adapted to the foregoing electronic device 100. The following may describe detailed steps of the method for selecting the influence indicators by using the automatic mechanism of the present embodiment with reference to devices and components of the electronic device 100.

First, the processor 110 obtains raw data, where the raw data includes a body-related variable and a plurality of to-be-measured indicators (step S202). In detail, the to-be-measured indicators included in the raw data are body components used for researching a specific physiological phenomenon, and the body-related variable is data correlated with the specific physiological phenomenon and obtained through measurement. According to the research of correlation factors of sarcopenia, for example, sarcopenia is a condition characterized by loss of appendicular skeletal muscle mass associated with aging and immobility, which indicates that there is a relationship between occurrence of sarcopenia and change of muscle mass. Because muscle is composed of proteins, a correlation between the proteins and the muscle mass that are in the body may be researched, and a protein related to the muscle mass is found. Herein, the to-be-measured indicators are, for example, different proteins. When a researcher intends to find the protein related to the muscle mass through research, the researcher may research, by using the body-related variable related to a muscle mass value, which protein may influence the muscle mass. For example, the body-related variable related to the muscle mass value is, for example, a grip strength, a lean body mass (LBM), an appendicular skeletal muscle mass (ASM), or a relative appendicular skeletal muscle mass (RASM, where a method for calculating the relative appendicular skeletal muscle mass is ASM/(height$^2$)).

Then, the processor 110 may set the body-related variable as a target parameter (step S204). Specifically, because the automatic mechanism provided in the present embodiment of the disclosure may use a plurality of machine learning models to help to select an important protein through screening, and a function of Y=f(X) needs to be constructed, the processor 110 may first set the body-related variable Y as the target parameter. By using the foregoing research of sarcopenia as an example, the body-related variable Y is, for example, a grip strength, a lean body mass, an appendicular skeletal muscle mass, or a relative appendicular skeletal muscle mass, and X in the function is, for example, to-be-measured indicators, to be specific, detected contents of thousands of proteins.

Subsequently, the processor 110 may input the body-related variable and the to-be-measured indicators into a plurality of validation models, and sort, according an output result of the validation models, the to-be-measured indicators to obtain ranking data (step S206). Specifically, the processor 110 may establish the validation models for predicting the target parameter (namely, the body-related variable Y) according to a machine learning method, predict importance of the to-be-measured indicators X relative to the body-related variable Y by using each established validation model, and sort, according to the importance of the to-be-measured indicators X relative to the body-related variable Y, the to-be-measured indicators X to generate the ranking data. For example, the processor 110 may establish the validation models through such as a regression method, a tree-based method, or a neural network model to calculate the importance of the to-be-measured indicators X in the function of Y=f(X). The regression method is, for example, linear regression, Lasso regression, ridge regression, support vector regression, or partial least square regression. The tree-based method is, for example, a decision tree method, or a random forest method. The neural network model is, for example, a deep neural network (DNN). After establishing the validation model, the processor 110 determines the importance of each to-be-measured indicator X by using a criterion of measuring the importance of the to-be-measured indicators X in each validation model. For example, the criterion that may determine the importance of the to-be-measured indicators X is, for example, a weight of the to-be-measured indicators X in the regression method or whether a p-value is significant, a level by which model accuracy declines after the to-be-measured indicators X are removed from the tree-based method, or a weight of a neuron in the neural network.

After obtaining data of the importance of the to-be-measured indicators X relative to the body-related variable Y, the processor 110 sorts the to-be-measured indicators X according to the obtained importance data, and generates the ranking data. A method for generating the ranking data is, for example, to rank the to-be-measured indicators X by using the importance of the to-be-measured indicators X or using a method for calculating the number of times. In an embodiment, the processor 110 may obtain rankings of the importance of the to-be-measured indicators X relative to the body-related variable predicted by each validation models, and respectively aggregate the rankings corresponding to the to-be-measured indicators X to generate the ranking data. In another embodiment, the processor 110 may further record the to-be-measured indicators X by using a manner of calculating the number of times. Specifically, after obtaining the rankings of the importance of the to-be-measured indicators X relative to the body-related variable predicted by each validation model, the processor 110 selects the to-be-measured indicators X from the rankings according to a preset number of rankings, and calculates quantities of times of selecting the to-be-measured indicators to generate the ranking data.

Then, the processor 110 calculates importance of the to-be-measured indicators by using a screening condition according to the ranking data to select a candidate indicator from the to-be-measured indicators (step S208). After calculating the ranking data through a plurality of validation models, the processor 110 may select the to-be-measured indicator X of which the ranking is the highest or the ranking is in front of a specific ranking as a to-be-measured indicator X with higher importance, and select the to-be-measured indicator (to-be-measured indicators) X as the candidate indicator.

In addition, the processor 110 may further perform screening according to other screening conditions or give more evidences to support selecting the candidate indicator from the to-be-measured indicators X. In an embodiment, the processor 110 may calculate the importance of the to-be-measured indicators X relative to the body-related variable Y by using the established validation models, and after sorting, according to the importance of the to-be-measured indicators X relative to the body-related variable Y, the to-be-measured indicators X to generate the ranking data, additionally limit the to-be-measured indicators X of which a correlation coefficient corresponding to the importance needs to be greater than a preset value and that can be selected to generate the ranking data. Specifically, the processor 110 may calculate a correlation coefficient between each of the to-be-measured indicators X and the body-related variable Y, and in the ranking data select, as the candidate indicator, the to-be-measured indicator X whose correlation coefficient relative to the body-related variable Y is greater than a preset threshold. The preset threshold may be determined through a series of prior analysis, and is stored in the storage device 120. For example, the preset threshold may be limited to 0.4.

In another embodiment, the processor 110 may select the candidate indicator by using an intersection set between a plurality of sets of ranking data. It should be noted that both the to-be-measured indicators X and the body-related variable Y are measured values, and units of the measured values are different, so that before step S206, the processor 110 may first standardize the body-related variable Y and the to-be-measured indicators X that are in the raw data as transformed data, then input the standardized transformed body-related variable and the standardized transformed to-be-measured indicators into the validation models, and sort, according to the output result of the validation model, the to-be-measured indicators to obtain the ranking data. Based on that, by performing data transformation on the raw data, the body-related variable and the to-be-measured indicators that are in the raw data are transformed into the transformed data meeting a model validation rule, and a requirement for a model validation method may be satisfied or a systematic error may be eliminated. The systematic error occurs because there is an error in a measuring instrument and measurement results of a same protein of a same person are different in different instruments. A data transformation method is, for example, standardization and/or log transformation. The standardization method may be represented as a formula (1), and the log transformation method may be represented as a formula (2):

$$x_{new} = \frac{X_{old} - \text{mean}(X_{old})}{\text{std}(X_{old})} \quad (1)$$

$$X_{new} = \log(X_{old}) \quad (2)$$

$X_{old}$ is the raw data before the to-be-measured indicators X are transformed, $X_{new}$ is the transformed data after the to-be-measured indicators X are transformed, $\text{mean}(X_{old})$ represents an average value of the raw data, $\text{std}(X_{old})$ represents a standard deviation of the raw data, and $\log(X_{old})$ represents a logarithm of the raw data.

In the method for selecting the candidate indicator by using the intersection set between the sets of ranking data, first, the processor 110 may standardize the body-related variable and the to-be-measured indicators X as the transformed data, and input the transformed data into the validation models to obtain transformed ranking data. The manner for obtaining the transformed ranking data by using the validation models is similar to the manner for obtaining the ranking data in step S206. Therefore, the descriptions thereof are omitted herein. Next, the processor 110 selects the candidate indicator from the to-be-measured indicators X according to the ranking data of the raw data and the rankings of the to-be-measured indicators X in the ranking data of the transformed data. In detail, the processor 110 may directly aggregate the rankings corresponding to the to-be-measured indicators X in the ranking data of the raw data and the ranking data of the transformed data, select the to-be-measured indicator X of which the ranking is the highest or the ranking is in front of a specific ranking as a to-be-measured indicator X with higher importance, and select the to-be-measured indicator (to-be-measured indicators) X as the candidate indicator. In another aspect, the processor 110 may alternatively first respectively select, as to-be-measured indicators X with higher importance, the to-be-measured indicator X of which the ranking is the highest or the ranking is in front of a specific ranking from the ranking data of the raw data and the to-be-measured indicator X of which the ranking is the highest or the ranking is in front of a specific ranking from the ranking data of the transformed data, and then select, in the two to-be-measured indicators X, the to-be-measured indicator X of which the number of times of being repeatedly selected is the highest or the number of times of being repeatedly selected is in front of a specific number of times of being selected as the candidate indicator, which is not limited in the disclosure.

In other words, the higher rankings of the to-be-measured indicators X in the ranking data and the transformed ranking data indicate higher importance. Based on that, an intersection set method may be used to select the to-be-measured indicator X of which the ranking is higher and that has most ranking intersection sets as the candidate indicator by cross-comparing the rankings of the to-be-measured indicators X in the ranking data and the transformed ranking data.

In another embodiment, the processor 110 may obtain, by using the foregoing model validation sorting method in step S206, a plurality of sets of ranking data of a plurality of body-related variables correlated with a same specific physiological phenomenon. Herein, the manner for selecting the candidate indicator by using the intersection set between the sets of ranking data is similar to the foregoing manner for selecting the candidate indicator in step S208. Therefore, the descriptions thereof are omitted herein.

Finally, the processor 110 calculates a correlation between the candidate indicator and the body-related variable to determine an influence indicator (step S210). After the foregoing steps, the processor 110 may select the candidate indicator which is the most important to the body-related variable Y from a plurality of to-be-measured indicators X. Then, the processor 110 may establish a model configured to perform validation to determine whether the correlation between the candidate indicator and the body-related variable Y meets a characteristic relationship between the two; that is, to determine, through the characteristic relationship, that the selected candidate indicator is the influence indicator which may be used for predicting the body-related variable Y. Specifically, the processor 110 validates the correlation between the candidate indicator and the body-related variable by using a statistical model to determine whether the candidate indicator is the influence indicator corresponding to the body-related variable. For example, model validation using a statistical method such as model accuracy or model significance is established to determine importance of the selected candidate indicator.

In another embodiment of the disclosure, reproducibility of an important indicator for the body-related variable is repeated by using a mechanism of randomly selecting data from the raw data. Therefore, a case that the candidate indicator selected through screen wins due to data skewness may be avoided. In addition, a plurality of sets of ranking data of the to-be-measured indicators X in a plurality of sets of randomly selected data are further predicted by using the validation models. Subsequently, weights of different validation models are determined by using the ranking data. Therefore, the obtained weights are fed back to step S206 in FIG. 2 to more accurately determine final ranking data of the to-be-measured indicators X.

Specifically, the processor 110 may randomly select a plurality of sets of sub-data from the raw data, and input the sub-data into the validation models to obtain a plurality of ranking data according to an output result of the validation models. Herein, the manner for selecting the candidate indicator by using the intersection set between the sets of ranking data is similar to the foregoing manner for selecting the candidate indicator in step S208. Therefore, the descriptions thereof are omitted herein. In another embodiment, a plurality of sets of randomly selected sub-data may be standardized, and the candidate indicator is selected by using the sets of ranking data obtained from a plurality of sets of standardized sub-data and by using an intersection set between the sets of ranking data obtained from a plurality of sets of sub-data.

Further, the processor 110 may further calculate importance of the to-be-measured indicators by using a screening condition according to the ranking data to select the candidate indicator from the to-be-measured indicators. Specifically, the processor 110 calculates an average characteristic number of each to-be-measured indicator X according to quantities of times of selecting the to-be-measured indicator X, in the ranking data corresponding to the sub-data, as the candidate indicator. Subsequently, the processor 110 determines the weight of the validation models according to a reciprocal of the average characteristic number, and determines the importance of the to-be-measured indicators X according to the weight of the validation models. For example, please refer to Table 1. Assuming that 10 sets of sub-data are selected randomly from the raw data, and after sorting is performed by using an output result of the validation models Lasso, RF, and SVR and the candidate indicator is selected, quantities of times of selecting to-be-measured indicators X1, X2, and X3 by each of the validation models are shown in Table 1. Herein, a manner of calculating the average characteristic number of the validation models is, for example, the total number of times of selecting the to-be-measured indicators/the number of sets of sub-data. A calculation result of the average characteristic number is shown in Table 1.

TABLE 1

| To-be-measured indicator | Lasso | RF | SVR | Average characteristic number |
|---|---|---|---|---|
| X1 | 6 | 7 | 8 | 21/10 = 2.1 |
| X2 | 5 | 6 | 3 | 14/10 = 1.4 |
| X3 | 9 | 4 | 9 | 22/10 = 2.2 |

A smaller average characteristic number corresponding to the validation models indicates a more important characteristic selected by the validation models. Therefore, the reciprocal of the average characteristic number may be used for determining an average number of times weight of each of the validation models. After the average number of times weight of each of the validation models is calculated, the number of times of selecting the to-be-measured indicator by each of the validation models is respectively multiplied by the average number of times weight of each of the validation models to obtain the importance of the to-be-measured indicator. Table 2 below takes a to-be-measured indicator X1 as an example. The importance of the to-be-measured indicator X1 is 6*W1+7*W2+8*W3. In the case of a to-be-measured indicator X2, the importance of the to-be-measured indicator X2 is 5*W1+6*W2+3*W3. By calculating the importance of the to-be-measured indicators X1 to X3, the processor 110 may select the candidate indicator from the to-be-measured indicators according to an importance result. The manner for selecting the candidate indicator is, for example, to select the to-be-measured indicator X of which the importance is the highest or the importance is in front of a specific ranking as the candidate indicator, which is not limited in the disclosure.

TABLE 2

| Validation model | Average number of times weight | Number of times of selecting a to-be-measured indicator X1 * average number of times weight |
|---|---|---|
| Lasso | W1 = (1/2.1)/(1/2.1 + 1/1.4 + 1/2.2) | 6*W1 |
| RF | W2 = (1/1.4)/(1/2.1 + 1/1.4 + 1/2.2) | 7*W2 |
| SVR | W3 = (1/2.2)/(1/2.1 + 1/1.4 + 1/2.2) | 8*W3 |

Figure 3:
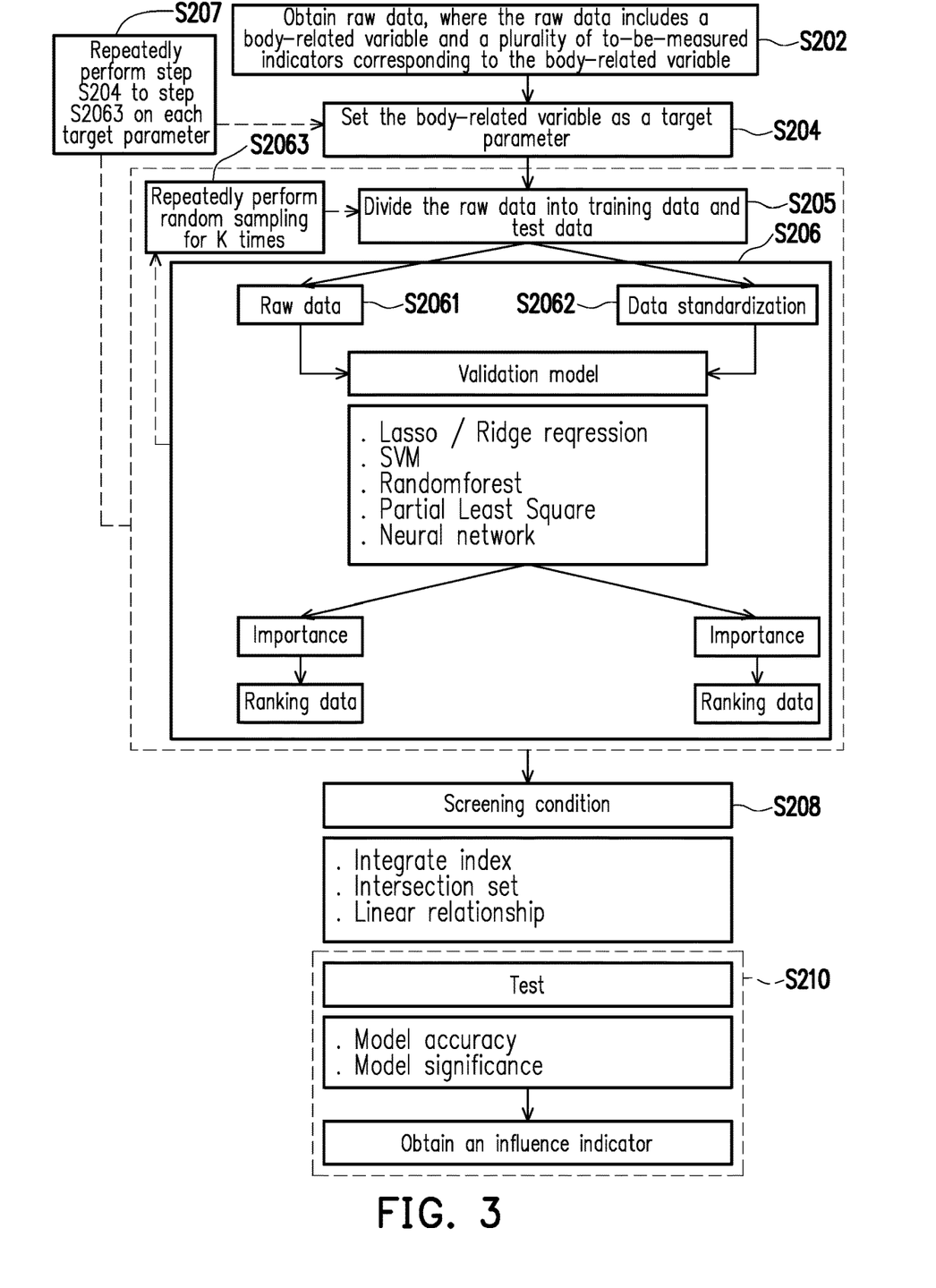
FIG. 3 is a flowchart of a method for selecting influence indicators by using an automatic mechanism according to an embodiment of the disclosure.

The following describes a specific implementation of the foregoing method of the disclosure with reference to embodiments. FIG. 3 is a flowchart of a method for selecting influence indicators by using an automatic mechanism according to an embodiment of the disclosure. The following embodiments describe, through research on a correlation factor of sarcopenia as an example, the method for selecting the influence indicators by using the automatic mechanism of the disclosure. It should be noted that the disclosure is not limited to being used for selecting the correlation factor of sarcopenia, and may also be used for selecting a plurality of to-be-measured indicators X correlated with a body-related variable Y of another specific physiological phenomenon (such as, another disease).

First, the processor 110 obtains raw data, where the raw data includes a body-related variable Y and a plurality of to-be-measured indicators X corresponding to the body-related variable Y (step S202). The body-related variable Y is set as a target parameter (step S204). In the present embodiment, the body-related variable Y may be, for example, a grip strength, a lean body mass, an appendicular skeletal muscle mass, or a relative appendicular skeletal muscle mass, and the to-be-measured indicators X include a plurality of types of proteins. Then, the processor 110 divides the raw data into training data and test data (step S205).

Subsequently, the processor 110 inputs the body-related variable and the to-be-measured indicators into a plurality of validation models, and sorts, according an output result of the validation models, the to-be-measured indicators to obtain ranking data (step S206). Specifically, in step S206, the processor 110 divides the training data into a raw data part (step S2061) and a data standardization part for standardizing the raw data (step S2062), and respectively inputs the raw data and the standardization data into the validation models to obtain the ranking data. In the present embodiment, the raw data after being calculated through the validation models Lasso, RF, and SVR is shown in Table 3, and Table 3 shows importance values of proteins X1 to X7 relative to each of the validation models. A ranking data generation method may be a ranking aggregation manner (shown in Table 4), or may be a manner of calculating the number of times (shown in Table 5). The detailed ranking data generation method is described above, and the descriptions thereof are omitted herein.

TABLE 3

| Protein | Lasso | RF | SVR |
|---|---|---|---|
| X1 | 0.8 | 0.9 | 1.7 |
| X2 | 2.3 | 0.8 | 5.8 |
| X3 | 0.1 | 0.7 | 2.3 |
| X4 | 0.05 | 0.6 | 0.2 |
| X5 | 0.001 | 0.5 | 0.1 |
| X6 | 5.3 | 0.4 | 2.8 |
| X7 | 1.2 | 0.3 | 5.6 |

TABLE 4

| Protein | Lasso | RF | SVR | Ranking aggregation |
|---|---|---|---|---|
| X1 | 4 | 1 | 5 | 10 |
| X2 | 2 | 2 | 1 | 5 |
| X3 | 5 | 3 | 4 | 12 |
| X4 | 6 | 4 | 6 | 16 |
| X5 | 7 | 5 | 7 | 19 |
| X6 | 1 | 6 | 3 | 10 |
| X7 | 3 | 7 | 2 | 12 |

TABLE 5

| Protein | Lasso | RF | SVR | Aggregation of quantities of times |
|---|---|---|---|---|
| X1 | 1 | 1 | 1 | 3 |
| X2 | 1 | 1 | 1 | 3 |
| X3 | 1 | 1 | 1 | 3 |
| X4 | 0 | 1 | 0 | 1 |
| X5 | 0 | 1 | 0 | 0 |
| X6 | 1 | 0 | 1 | 2 |
| X7 | 1 | 0 | 1 | 2 |

In the present embodiment, the processor 110 may perform random sampling for K times on the raw data to select a plurality of sets of sub-data (step S2063), and perform model validation on the sets of sub-data again to obtain a plurality of sets of ranking data. Alternatively, the processor 110 may repeatedly perform step S204 to step S2063 on all target parameters (namely, different body-related variables), so as to obtain the sets of ranking data (step S207). Herein, whether to perform random sampling or repeatedly perform the step of obtaining the sets of ranking data on different body-related variables may be designed and adjusted by a person skilled in the art, which is not limited in the disclosure.

Then, the processor 110 calculates importance of the to-be-measured indicators by using a screening condition according to the ranking data to select a candidate indicator from the to-be-measured indicators (step S208). For step S208, reference may be made to the content of the corresponding step in FIG. 2, and the descriptions thereof are omitted herein. In the present embodiment, the processor 110 selects a protein Q7 as the candidate indicator.

Finally, the processor 110 calculates a correlation between the candidate indicator and the body-related variable to determine an influence indicator (step S210). Specifically, the processor 110 determines whether the selected protein Q7 is the influence indicator corresponding to the body-related variable by using the test data. In an embodiment, the model accuracy is, for example, to establish a logical model between the protein Q7 and a specific physiological phenomenon (for example, sarcopenia). An example of a model establishment result is shown in Table 6. Herein, an odds ratio of the protein Q7 is positive, indicating that the selected protein Q7 and the specific physiological phenomenon are in a positive relationship. In this case, it may be determined that the selected protein Q7 is the influence indicator of sarcopenia.

TABLE 6

|  | Odds ratio |
|---|---|
| Log(Q7) | 1.71 |
| Age | 1.07 |
| Gender | 0.84 |

In another embodiment, the model significance is, for example, to establish a logical model between a candidate indicator Q7 (for example, a protein) and a physiological phenomenon (for example, asthenic syndrome) similar to the specific physiological phenomenon (for example, sarcopenia). An example of a model establishment result is shown in Table 7. Herein, an odds ratio of the protein Q7 is positive and a p-value is less than 0.05, indicating that the selected protein Q7 and the asthenic syndrome are in a positive relationship. The asthenic syndrome and sarcopenia have a similar situation of muscle mass reduction, and therefore in this prediction result, it may be inferred that the selected protein Q7 is the influence indicator of sarcopenia.

TABLE 7

|  | Odds ratio | P-value |
|---|---|---|
| Log(Q7) | 7.23 | 0.047 |
| Age | 1.24 | <0.001 |
| Gender | 0.97 | 0.955 |

In another embodiment, the model significance is, for example, to establish a linear model between a candidate indicator Q7 (for example, a protein) and a value of a subject related to muscle mass (for example, a grip strength, a walking speed, a lean body mass, an appendicular skeletal muscle mass, or a relative appendicular skeletal muscle mass). An example of a model establishment result is shown in Table 8 and Table 9. It may be seen from Table 8 and Table 9 that a correlation coefficient between the protein Q7 and the grip strength, the walking speed, the lean body mass, the appendicular skeletal muscle mass, or the relative appendicular skeletal muscle mass is negative, and a p-value is less than 0.05. The prediction result indicates that the value related to the muscle mass and the protein Q7 are in a negative relationship. In other words, a larger value of the protein Q7 indicates a smaller value related to the muscle mass. Sarcopenia has a situation of muscle mass reduction, and therefore in this prediction result, it may be determined that the selected protein Q7 is the influence indicator of sarcopenia.

TABLE 8

| | Y | | | |
|---|---|---|---|---|
| | Log(grip strength) | | Log(walking speed) | |
| X | Correlation coefficient | P-value | Correlation coefficient | P-value |
| Log(Q7) | −0.198 | 0.010 | −0.2 | 0.103 |
| Age | −0.016 | <0.001 | −0.028 | <0.001 |
| Gender | 0.472 | <0.001 | 0.168 | 0.005 |

TABLE 9

| | Y | | | | | |
|---|---|---|---|---|---|---|
| | Log(LBM) | | Log(ASM) | | Log(RASM) | |
| X | Correlation coefficient | P-value | Correlation coefficient | P-value | Correlation coefficient | P-value |
| Log(Q7) | −0.078 | 0.037 | −0.084 | 0.05 | −0.07 | 0.045 |
| Age | −0.078 | 0.011 | −0.005 | <0.001 | −0.002 | 0.051 |
| Gender | 0.31 | <0.001 | 0.365 | <0.001 | 0.219 | <0.001 |

In still another embodiment, the model grouping significance is, for example, to divide values related to the muscle mass (for example, a grip strength, a walking speed, a lean body mass, an appendicular skeletal muscle mass, and a relative appendicular skeletal muscle mass) into high and low groups, and validate whether there is a significant difference between contents of the candidate indicators Q7 (for example, proteins) of the two groups.

Figure 4A:
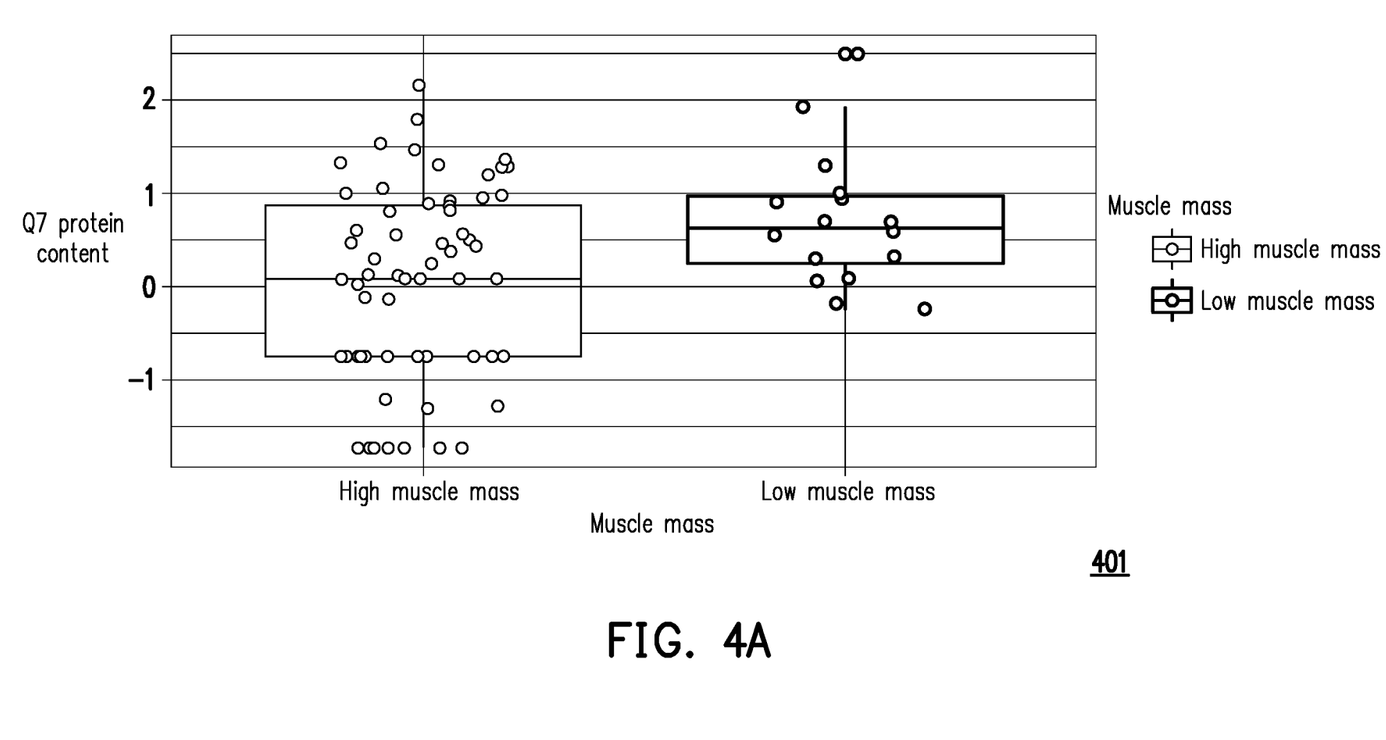
FIG. 4A shows an example of validating significance of a content of a male protein Q7 according to an embodiment of the disclosure.

The appendicular skeletal muscle mass and a male subject are used as an example. FIG. 4A shows an example of validating significance of a content of a male protein Q7 according to an embodiment of the disclosure. With reference to a grouping box plot 401 in FIG. 4A, in the example, a T-value of a T validation result between a high muscle mass and a low muscle mass is 3.1579, that is, the T validation result has a significant difference. Therefore, a group of the high muscle mass is displayed, and the content of the protein Q7 of the group of the high muscle mass is lower. In other words, the prediction result indicates that the content of the protein Q7 of a group of the low muscle mass is higher. Sarcopenia has a situation of muscle mass reduction, and therefore in this prediction result, it may be determined that the selected protein Q7 is the influence indicator of sarcopenia.

Figure 4B:
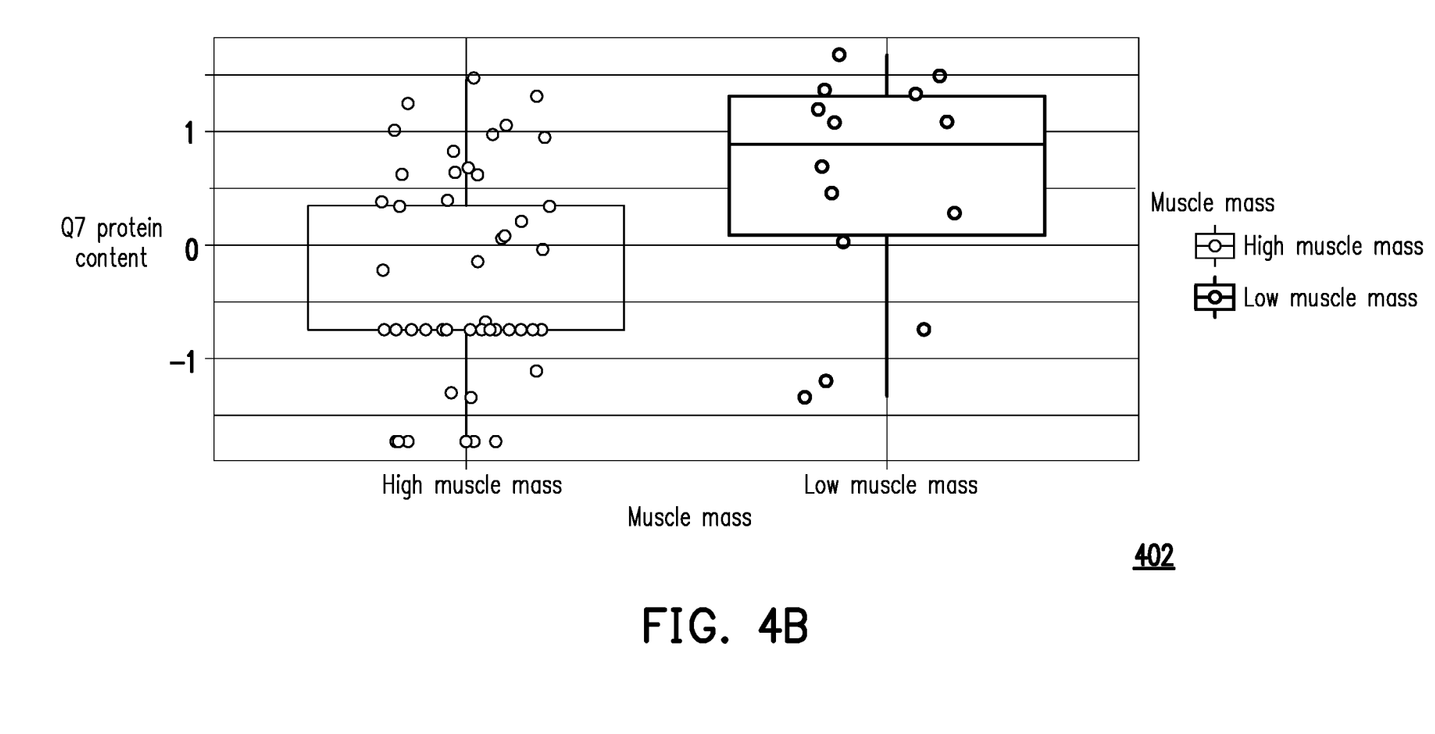
FIG. 4B shows an example of validating significance of a content of a female protein Q7 according to an embodiment of the disclosure.

The appendicular skeletal muscle mass and a female subject are used as an example. FIG. 4B shows an example of validating significance of a content of a female protein Q7 according to an embodiment of the disclosure. With reference to a grouping box plot 402 in FIG. 4B, in the example, a T-value of a T validation result between a high muscle mass and a low muscle mass is 3.0243, that is, the T validation result has a significant difference. Therefore, a group of the high muscle mass is displayed, and the content of the protein Q7 of the group of the high muscle mass is lower. In other words, the prediction result indicates that the content of the protein Q7 of a group of the low muscle mass is higher. Sarcopenia has a situation of muscle mass reduction, and therefore in this prediction result, it may be determined that the selected protein Q7 is the influence indicator of sarcopenia.

In conclusion, in the embodiments of the disclosure, by using different validation models and randomly selecting different samples, a main to-be-measured indicator that has influence on predicting the body-related variable is automatically found from the to-be-measured indicators. Therefore, the influence indicator which has a correlation with the body-related variable can be selected from the to-be-measured indicators to avoid a large number of experiments that take time and effort, thereby automatically selecting the influence indicator.

What is claimed is:

1. A method for selecting influence indicators by using an automatic mechanism, adapted to an electronic device and comprising:
   obtaining raw data, wherein the raw data comprises a body-related variable and a plurality of to-be-measured indicators corresponding to the body-related variable, wherein the plurality of to-be-measured indicators comprise a plurality of proteins;
   setting the body-related variable as a target parameter;
   inputting the body-related variable and the to-be-measured indicators into a plurality of validation models, and sorting, according to an output result of the validation models, the to-be-measured indicators to obtain ranking data;
   calculating importance of the to-be-measured indicators by using a screening condition according to the ranking data to select a candidate indicator from the to-be-measured indicators;
   calculating a correlation between the candidate indicator and the body-related variable to determine an influence indicator; and
   outputting the influence indicator.

2. The method for selecting the influence indicators by using the automatic mechanism according to claim 1, wherein the step of inputting the body-related variable and the to-be-measured indicators into the validation models, and sorting, according to the output result of the validation models, the to-be-measured indicators to obtain the ranking data comprises:
   predicting the importance of the to-be-measured indicators relative to the body-related variable by using the validation models; and sorting, according to the importance of the to-be-measured indicators relative to the body-related variable, the to-be-measured indicators to generate the ranking data.

3. The method for selecting the influence indicators by using the automatic mechanism according to claim 2, wherein the step of sorting, according to the importance of the to-be-measured indicators relative to the body-related variable, the to-be-measured indicators to generate the ranking data comprises:
   obtaining rankings of the importance of the to-be-measured indicators relative to the body-related variable; and
   respectively aggregating the rankings corresponding to the to-be-measured indicators to generate the ranking data.

4. The method for selecting the influence indicators by using the automatic mechanism according to claim 2, wherein the step of sorting, according to the importance of the to-be-measured indicators relative to the body-related variable, the to-be-measured indicators to generate the ranking data comprises:
   obtaining rankings of the importance of the to-be-measured indicators relative to the body-related variable;
   selecting the to-be-measured indicators from the rankings according to a preset number of rankings; and
   calculating the number of times of selecting the to-be-measured indicators to generate the ranking data.

5. The method for selecting the influence indicators by using the automatic mechanism according to claim 1, wherein before the step of inputting the body-related variable and the to-be-measured indicators into the validation models, and sorting, according to the output result of the validation models, the to-be-measured indicators to obtain the ranking data, the method further comprises:
   standardizing the body-related variable and the to-be-measured indicators in the raw data as transformed data; and
   inputting the transformed data into the validation models to obtain transformed ranking data.

6. The method for selecting the influence indicators by using the automatic mechanism according to claim 5, wherein the step of calculating the importance of the to-be-measured indicators by using the screening condition according to the ranking data to select the candidate indicator from the to-be-measured indicators comprises:
   selecting the candidate indicator from the to-be-measured indicators according to rankings of the to-be-measured indicators in the ranking data and the transformed ranking data.

7. The method for selecting the influence indicators by using the automatic mechanism according to claim 1, wherein the step of calculating the importance of the to-be-measured indicators by using the screening condition according to the ranking data to select the candidate indicator from the to-be-measured indicators comprises:
   in the ranking data, selecting, as the candidate indicator, a to-be-measured indicator whose correlation coefficient relative to the body-related variable is greater than a preset threshold.

8. The method for selecting the influence indicators by using the automatic mechanism according to claim 1, wherein the step of calculating the correlation between the candidate indicator and the body-related variable to determine the influence indicator comprises:
   validating the correlation between the candidate indicator and the body-related variable by using a statistical model to determine whether the candidate indicator is the influence indicator corresponding to the body-related variable.

9. The method for selecting the influence indicators by using the automatic mechanism according to claim 1, further comprising:
   randomly selecting a plurality of sets of sub-data from the raw data, and inputting the sub-data into the validation models to obtain a plurality of ranking data according to an output result of the validation models;
   calculating an average characteristic number of each of he to-be-measured indicators according to the number of times of selecting the to-be-measured indicator as the candidate indicator in the ranking data corresponding to the sub-data;
   determining a weight of the validation models according to a reciprocal of the average characteristic number; and
   determining the importance of the to-be-measured indicators according to the weight of the validation models.

10. An electronic device, comprising:
    a storage device, storing at least one instruction; and
    a processor, coupled to the storage device and configured to execute the at least one instruction to:
        obtain raw data, wherein the raw data comprises a body-related variable and a plurality of to-be-measured indicators corresponding to the body-related variable;
        set the body-related variable as a target parameter;
        input the body-related variable and the to-be-measured indicators into a plurality of validation models, and sort, according to an output result of the validation models, the to-be-measured indicators to obtain ranking data;
        calculate importance of the to-be-measured indicators by using a screening condition according to the ranking data to select a candidate indicator from the to-be-measured indicators; and
        calculate a correlation between the candidate indicator and the body-related variable to determine an influence indicator.

* * * * *